(12) United States Patent
Rosenbaum et al.

(10) Patent No.: US 7,947,179 B2
(45) Date of Patent: May 24, 2011

(54) DIALYSIS SYSTEM

(75) Inventors: Benjamin P. Rosenbaum, Nashville, TN (US); Stephen R. Ash, Lafayette, IN (US); David J. Carr, West Lafayette, IN (US)

(73) Assignee: Renal Solutions, Inc., Warrendale, PA (US)

(*) Notice: Subject to any disclaimer, the term of this patent is extended or adjusted under 35 U.S.C. 154(b) by 0 days.

(21) Appl. No.: 12/827,617

(22) Filed: Jun. 30, 2010

(65) Prior Publication Data
US 2010/0326911 A1    Dec. 30, 2010

Related U.S. Application Data

(62) Division of application No. 11/148,928, filed on Jun. 9, 2005, now Pat. No. 7,776,210.

(60) Provisional application No. 60/578,257, filed on Jun. 9, 2004.

(51) Int. Cl.
*B01D 61/34* (2006.01)

(52) U.S. Cl. ....... 210/638; 210/96.2; 210/130; 210/259; 210/266; 210/645; 210/646

(58) Field of Classification Search .................. 210/646, 210/96.2, 321.71, 259, 266, 130, 433.1
See application file for complete search history.

(56) References Cited

U.S. PATENT DOCUMENTS 7,033,498 B2 * 4/2006 Wong ................ 210/321.71
2004/0019312 A1 * 1/2004 Childers et al. ............ 604/4.01

* cited by examiner

*Primary Examiner* — Krishnan S Menon
*Assistant Examiner* — Dirk Bass
(74) *Attorney, Agent, or Firm* — Fish & Richardson P.C.

(57) ABSTRACT

A dialysate fluid circulation apparatus includes a dialyzer, a first housing and a second housing. The first housing contains material capable of releasing sodium into dialysate fluid flowing through the first housing. The second housing contains material capable of binding sodium ions from dialysate fluid flowing through the second housing. Hydraulic conduit sections are configured to extend between the dialyzer, the first housing, and the second housing to connect the dialyzer with the housings in a primary flow path for dialysate fluid to flow from the dialyzer to the first housing, from the first housing to the second housing, and from the second housing back to the dialyzer.

14 Claims, 4 Drawing Sheets

DIALYSIS SYSTEM

RELATED APPLICATIONS

This application is a divisional (and claims the benefit of priority under 35 U.S.C. §121) of U.S. application Ser. No. 11/148,928, filed Jun. 9, 2005, now U.S. Pat. No. 7,776,210 which claims the benefit of U.S. Provisional Application No. 60/578,257, filed Jun. 9, 2004. The disclosure of the prior applications is considered part of (and is incorporated by reference in) the disclosure of this application.

FIELD

Systems and methods for the dialysis of mammalian blood systems.

BACKGROUND

A dialysis system typically includes a hydraulic system for circulating blood, a hydraulic system for circulating dialysate fluid, and a semi-permeable membrane. The blood system and the dialysate fluid system have fluid flow paths that extend past the membrane on opposite sides of the membrane. Urea and other blood components, but not blood cells, travel across the membrane from the blood side to the dialysate side as the blood and dialysate fluid both flow past the membrane.

In the oldest type of dialysis systems, the dialysate fluid, which is water infused with minerals and other essential blood components, is continually directed to flow past a membrane along a flow path extending from a source to a waste receptacle. This type of continuous flow may require hundreds of liters of dialysate fluid. More current dialysis systems recycle the exposed dialysate fluid rather than send it to a waste receptacle. Dialysis systems that recycle dialysate fluid have a dialysate fluid volume on the order of 6-10 liters.

In order to recycle dialysate fluid, urea and other blood waste compounds must be removed before the fluid is again passed by the membrane. One way to accomplish the removal of urea, for example, is to expose the urea to urease, which breaks the urea molecules down into ammonium ions and carbonate. The ammonium ions, which are toxic and should not be exposed to the membrane, can be bound, for example, by zirconium phosphate. In this case, zirconium phosphate acts as an ion exchanger and exchanges ammonium ions for sodium ions.

Because sodium is released by commercially available systems in the urea removal process, the sodium ion concentration in the dialysate fluid rises during the course of a dialysis treatment. The 6-10 liter systems have the capacity to dilute rising sodium ion levels such that the sodium ion concentration does not reach physiologically unacceptable levels. These 6-10 liter systems have the added benefit of being transportable relative to continuous flow type systems that require a source of high purity water used to make dialysate fluid in high volumes. For example, with the proper training and supervision, 6-10 liter systems can be easily adapted for use in a home environment without extensive equipment installation or home modification.

Another effect of dialysis treatment is the removal of excess water from the blood. Dialysis is often required because a patient's renal function is reduced, which means, in part, that the patient's ability to remove water from the blood is similarly reduced. In 6-10 liter systems, the total hydraulic fluid volume is expandable. Because the total volume is expandable, water can be removed from the patient into the dialysate system during dialysis. Water transport can be accomplished by creating a pressure differential between the blood side and the dialysate side such that water will flow from the blood side across the membrane to the dialysate side in a controlled manner.

SUMMARY

A dialysate fluid circulation apparatus includes a dialyzer, a first housing and a second housing. The first housing contains material capable of releasing sodium into dialysate fluid flowing through the first housing. The second housing contains material capable of binding sodium ions from dialysate fluid flowing through the second housing. Hydraulic conduit sections are configured to extend between the dialyzer, the first housing, and the second housing to connect the dialyzer with the housings in a primary flow path for dialysate fluid to flow from the dialyzer to the first housing, from the first housing to the second housing, and from the second housing back to the dialyzer.

Preferably, the hydraulic conduit sections are further configured to define a bypass flow path for dialysate fluid to bypass the second housing by flowing from the first housing back to the dialyzer. A fluid flow regulator is operative to control the flows of dialysate fluid along the primary and bypass flow paths. A controller actuates the regulator in response to input from a meter that is operative to indicate the sodium ion concentration in the dialysate fluid emerging from the first housing.

Summarized differently, an apparatus is configured for use with a dialysate fluid system that includes material capable of releasing sodium into dialysate fluid flowing in the system. The apparatus comprises a housing containing material capable of binding sodium ions from dialysate fluid flowing through the housing.

A method includes the steps of passing dialysate fluid through a dialyzer, conveying the dialysate fluid from the dialyzer to a first housing containing material that releases sodium into the dialysate fluid, and passing the dialysate fluid through the material in the first housing. The method further includes the steps of conveying the dialysate fluid from the first housing to a second housing containing material that binds sodium ions from the dialysate fluid, passing the dialysate fluid through the material in the second housing, and conveying the dialysate fluid from the second housing back to the dialyzer.

Preferably, the method includes the additional steps of measuring sodium ion concentration in the dialysate fluid emerging from the first housing, and directing a portion of the dialysate fluid to bypass the second housing if the measured sodium ion concentration is not greater than a predetermined level.

DETAILED DESCRIPTION

Figure 1:
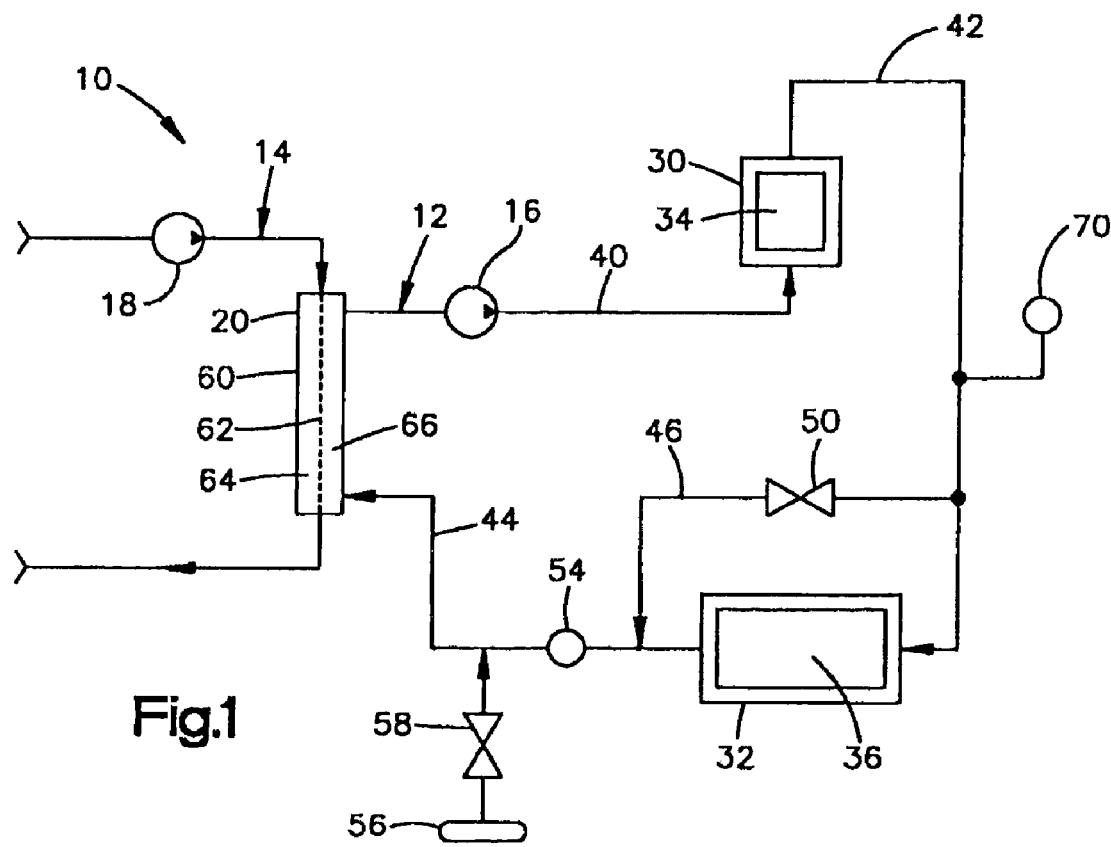
FIG. 1 is a schematic view showing parts of a dialysis system.

The dialysis systems shown schematically in the drawings have parts that are examples of the elements recited in the apparatus claims, and can be operated in steps that are examples of the elements recited in the method claims. The illustrated systems thus include examples of how a person of ordinary skill in the art can make and use the claimed invention. They are described here to meet the enablement and best mode requirements of the patent statute without imposing limitations that are not recited in the claims.

As shown in FIG. 1, an example of a dialysis system 10 includes a pair of distinct hydraulic systems 12 and 14. The first hydraulic system 12 contains dialysate fluid. The second hydraulic system 14, which is shown partially, contains a patient's blood. A first pump 16 drives dialysate fluid through the dialysate fluid system 12. A second pump 18 drives blood through the blood system 14. The dialysate fluid system 12 and the blood system 14 overlap at a dialyzer 20, but are otherwise separate from each other. Impurities, including urea, are drawn out of the blood and into the dialysate fluid as the blood and dialysate fluid both flow through the dialyzer 20.

The dialysate fluid system 12 further includes a first housing 30 and a second housing 32. As described more fully below, the first housing 30 contains material 34 that decomposes urea from the dialysate fluid flowing through the first housing 30. The decomposition of urea may produce undesirable amounts of sodium. The second housing 32 contains material that binds sodium ions from the dialysate fluid flowing through the second housing 32.

A first conduit 40 extends from the dialyzer 20 to the first housing 30. A second conduit 42 extends from the first housing 30 to the second housing 32. A third conduit 44 extends from the second housing 32 back to the dialyzer 20. In this arrangement, the first, second and third conduits 40, 42 and 44 complete a primary flow path along which the dialysate fluid can circulate through the system 12 in a clockwise direction, as viewed in FIG. 1 under the influence of the pump 16. Specifically, the primary flow path includes the dialyzer 20, the first conduit 40, the first housing 30, the second conduit 42, the second housing 32, and the third conduit 44.

As further shown schematically in FIG. 1, a fourth conduit 46 bypasses the second housing 32. This provides a bypass flow path that differs from the primary flow path by omitting the second housing 32. The bypass flow path thus includes the dialyzer 20, the first conduit 40, the first housing 30, a portion of the second conduit 42, the fourth conduit 46, and a portion of the third conduit 44.

A bypass flow regulator 50 controls the flow of dialysate fluid through the fourth conduit 46. The regulator 50 could be a simple clamp or an on/off valve, but preferably is a valve that is shiftable between a closed condition and a range of open conditions.

Other components of the dialysate fluid system 12 include a bubble remover 54 and an infusate reservoir 56. The bubble remover 54 is operative to remove gas bubbles from the dialysate fluid. The infusate reservoir 56 has a pump 58 for delivering infusate to the system 12. The infusate is a solution containing minerals and other blood components that might need to be added or replenished in the dialysate fluid.

The dialyzer 12 is a known device including a housing 60 containing a semi-permeable membrane 62. The membrane 62 is disposed between the blood system 14 and the dialysate fluid system 12 such that blood flows in one direction through the housing 60 along the blood side 64 of the membrane 62, and dialysate fluid flows in the opposite direction through the housing 60 on the dialysate side 66 of the membrane 62. Urea and other blood impurities are small enough to pass through the membrane 62 from the blood side 64 to the dialysate side 66, but blood cells and other blood components are too large to pass through the membrane 62 and are retained in the blood.

Several factors affect the diffusion of blood impurities from the blood side 64 to the dialysate side 66 of the membrane 62. One factor is the concentration gradient for each impurity between the blood side 64 and the dialysate side 66. If the concentration of an impurity on the blood side 64 is higher than the concentration of the impurity on the dialysate side 66, the impurity will diffuse across the membrane 62 in order to equalize the concentration.

Another factor affecting the diffusion of blood impurities across the membrane 62 is a pressure differential across the membrane 62. If the hydraulic fluid pressure is higher on one side of the membrane 62, fluid will flow across the membrane from the higher pressure side to the lower pressure side in order to equalize the pressure across the membrane 62. Fluid flow across the membrane 62 due to pressure differences is not selective in terms of the components flowing across the membrane. Therefore, water molecules, minerals, and other smaller blood components will flow across the membrane 62 under the influence of a sufficient pressure gradient. A pressure-driven flow across a membrane from the blood side to the dialysate side is known as ultrafiltration.

The first housing 30 downstream of the dialyzer 20 preferably is a sorbent-type cartridge containing material 34 that decomposes urea and releases sodium. Sorbent cartridges are well known. A typical sorbent cartridge contains several layers of materials including, for example, one or more layers of activated carbon, urease, zirconium phosphate, and/or zirconium oxide. In such a cartridge, urease breaks urea down into ammonium and carbonate. The zirconium phosphate layer, or a similar material, binds the ammonium in exchange for sodium ions. The different layers of the sorbent cartridge will, of course, bind other compounds, minerals, and ions as well. Some of these other compounds, minerals, and ions may also cause sodium to be released. The combination of these materials allows water suitable for drinking to be charged into the system for use as dialysate fluid.

The second housing 32 downstream of the dialyzer 20 contains the material 36 that will bind sodium ions. One type of compatible material may release protons or some other physiologically harmless or less harmful counter ion in exchange for sodium ions as the sodium ions are adsorbed. Such materials will typically bind other ions in addition to sodium ions. One example of a compatible material is a mixed bed ion exchange resin. A mixed bed ion exchange resin in this case comprises a cation exchange resin and an anionic exchange resin that are intimately mixed and contained in the same housing. Intimate mixing of the cation and anion exchange resins provides a constant, large concentration gradient that drives mass transfer of the ionic species from solution to adsorb to the resin surface in exchange for the complementary cationic and anionic species. The beneficial concentration gradient is constantly available as long as the exchange resins have ion binding capacity. The ratio of cation exchange resin to anion exchange resin can be varied to obtain the most efficient sodium binding possible.

Many resin properties, such as capacity, the degree of cross-linking, the physical and chemical nature of the polymer matrix, and the number of ions in the resin may be considered in the choice of resins used in the second housing 32. An example of a cation exchange resin is a proton loaded sulfonated spherical styrene-divinylbenzene copolymer. An example of an anion exchange resin is a hydroxide loaded spherical quaternary amine styrene-divinylbenzene copolymer. Additional examples of ion exchange materials that can be used include, but are not intended to be limited to, proton loaded zirconium phosphate (cation exchange material) and hydroxide loaded zirconium oxide (anion exchange material).

Ion exchange materials are often rated based on their theoretical capacity of a particular ion or molecule. For example, a particular volume of material might have a theoretical capacity of 488 grains of NaCl (541 mEq of NaCl). The desired sodium ion binding capacity of the material 36 used in the second housing 32 can be established by evaluating the amount of sodium predicted to be released by the material 34 in the first housing 30 during dialysis. For example, the sodium ion binding capacity of the material 36 used in the second housing 32 could be less than or equal to about 800 mEq, less than or equal to about 600 mEq, or less than or equal to about 500 mEq depending on the predicted sodium release from the material 34 in the first housing 30.

As an alternative to the mixed bed ion exchange resin, the cation and anion exchange resins may be separately maintained in the second housing 32. The cation exchange resin might occupy the first half of the second housing 32 and the anion exchange resin might occupy the second half of the second housing 32. The ratio of cation to anion resins can be varied in this resin configuration.

Additionally, the second housing 32 may comprise two separate compartments connected in parallel or in series where one of the housings contains a cation exchange resin and the other housing contains an anion exchange resin. Separating the cation and anion exchange resins into different housing compartments also allows the mass of anion to cation exchange materials to be independently altered, thereby varying the ratio of anion to cation exchange materials. The overall ion binding capacity of cation and anion exchange resins separated into housing compartments connected in parallel or series may not be as great as a mixed bed application in a single housing compartment. Thus, if the dialysis system design calls for a second compartment that binds sodium ions to have the smallest footprint possible, then a mixed bed ion exchange system might be the most appropriate choice. However, if size is not a constraint and the ability to vary the anion to cation exchange resin ratio is desired, then a parallel or series configuration might be utilized.

The dialysate fluid system 12 further includes a meter 70 capable of indicating sodium ion concentration in the dialysis fluid emerging from the first housing 30. The meter 70 may be, for example, a sodium ion selective electrode, which would measure sodium ion concentration directly. However, the meter 70 does not need to be capable of measuring sodium ion concentration directly. For example, the meter 70 may be a conductivity meter or a pH meter. In the case of a conductivity meter or a pH meter, the total ion concentration in solution is measured. Such measurements, if taken over time, can provide an indication of changes in sodium ion concentration. Inductive, i.e., non-contact, conductivity measurements also are possible.

Figure 2:
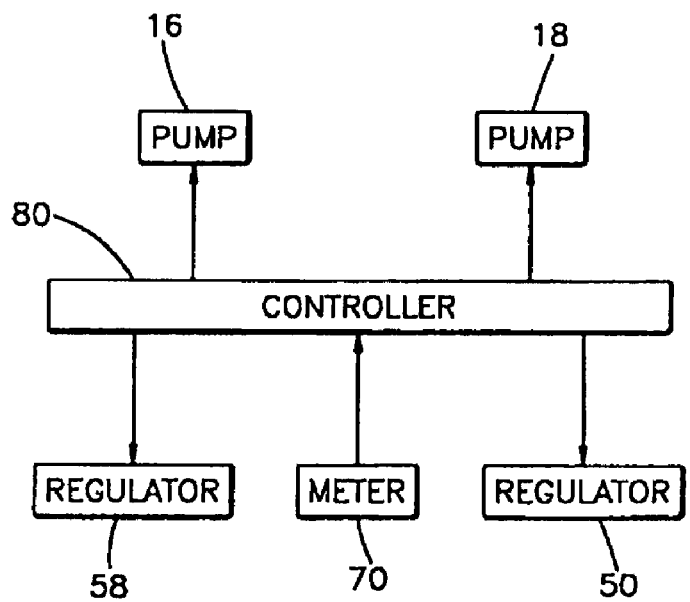
FIG. 2 is a schematic view showing parts of the system of FIG. 1.

As shown schematically in FIG. 2, the dialysis system 10 further includes a controller 80 that is operatively interconnected with the pumps 16 and 18, the regulator 50 in the bypass conduit 46, and the sodium meter 70. The controller 80 has hardware and/or software configured for operation of those components 16, 18, 50 and 70, and may comprise any suitable programmable logic controller or other control device, or combination of control devices, that is programmed or otherwise configured to perform as recited in the claims.

The dialysate fluid system 12 may also include, for example, various valves for starting and stopping fluid flow, fluid pumps or other fluid flow generating devices, flow meters for detecting flow and measuring flow rates, a dialysate fluid heater for controlling the temperature of the dialysate, an ammonia and/or ammonium ion monitoring device to detect ammonia molecules and/or ammonium ions in the dialysate fluid, and other known devices that may take part in the performance of a dialysis treatment on a patient. Such other devices, which are well known to those skilled in the art, are omitted from the drawings for clarity of illustration.

In operation, the controller 80 initiates a dialysis treatment by starting the pumps 16 and 18 to initiate circulating flows of dialysate fluid and blood through their respective hydraulic systems 12 and 14. The dialyzer 60 then causes urea and other impurities to be transferred from the blood system 14 to the dialysate fluid system 12. As the dialysate fluid traverses that system 12, it flows through the first conduit 40 from the dialyzer 60 to the first housing 30. The dialysate fluid then encounters the material 36 as it flows through the first housing 30, whereupon the decomposition of urea from the dialysate fluid causes sodium to be added to the fluid. The concentration of sodium in the fluid emerging from the first housing 30 is detected by the meter 70 and is input to the controller 80.

The controller 80 is operable in differing modes in accordance with the sodium concentration indicated by the meter 70. For example, if the sodium concentration indicated by the meter 70 is not greater than a predetermined threshold level, the controller 80 operates in a bypass mode in which the regulator 50 is maintained in a fully open condition. This enables a significant portion of the dialysate fluid to bypass the second housing 32 by flowing through the bypass conduit 46, and thereby to bypass the sodium-binding material 36 that would otherwise act upon that portion of the dialysate fluid. The threshold level of sodium concentration could be, for example, about 145 mEq/L, or any other level considered to define a physiologically acceptable concentration of sodium, such as levels of about 150, 155, or 160 mEq/L.

If the sodium concentration indicated by the meter 70 is at or above the threshold level, the controller 80 shifts to a partial bypass mode of operation by shifting the regulator 50 from the fully open condition to lesser open condition. This permits a lesser proportion of the dialysate fluid to flow through the bypass conduit 46, with a correspondingly greater proportion of the dialysate fluid flowing through the second housing 32 for removal of sodium.

Preferably, the controller 80 operates in the partial bypass mode with reference to a predetermined, manageable range of sodium levels above the threshold level. The manageable range of sodium concentration levels could be, for example, from about 90 mEq/L to about 160 mEq/L. The controller 80 can shift the regulator 50 through a range of open conditions that corresponds to the manageable range of sodium levels. Accordingly, the proportion of dialysate fluid directed to the second housing 32 is increased or decreased in direct relationship to the detected level of sodium as that level increases or decreases throughout the manageable range. If the detected level of sodium concentration exceeds the maximum manageable level, the controller 80 shifts the regulator 50 to a closed condition for operation in a mode in which none of the dialysate fluid is permitted to bypass the second housing 32 as it flows from the first housing 30 back to the dialyzer 60.

The foregoing example of a dialysate fluid system 12 is configured to be charged with dialysate fluid, and to be operated without a significant increase in the volume of fluid contained in the system 12 throughout a dialysis treatment. The dialysate fluid system 12 thus has a non-expandable volume. More specifically, the dialyzer 20, housings 30 and 32, conduits 40-46, and other hydraulic system components shown in the drawings, as well as any additional hydraulic devices that may be included as noted above, are each configured with only a single volumetric capacity to contain or convey dialysate fluid. This constrains the volume of the system 12 such that a significant volume of water is prevented from passing from the blood side 64 of the dialyzer membrane 62 to the dialysate side 66. Preferably, the non-expandable volume of the system 12 is less than or equal to about 3 liters. The non-expandable volume could alternatively be less than or equal to about 2 liters, less than or equal to about 1.5 liters, or about 1 liter. These are relatively small volumes that enable the dialysis system 10 as a whole to be relatively small, and preferably to be small enough to be contained in a portable housing such as a backpack or the like.

Figure 3:
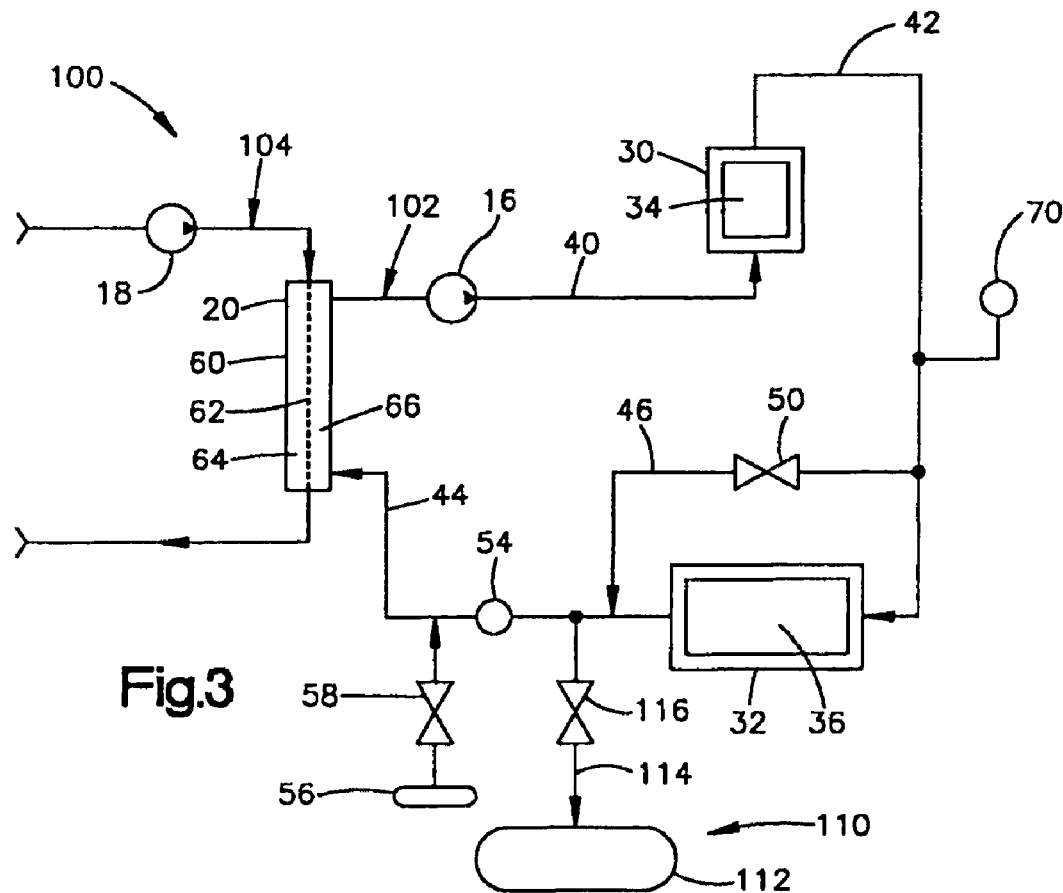
FIG. 3 is a schematic view showing parts of another dialysis system.
Figure 4:
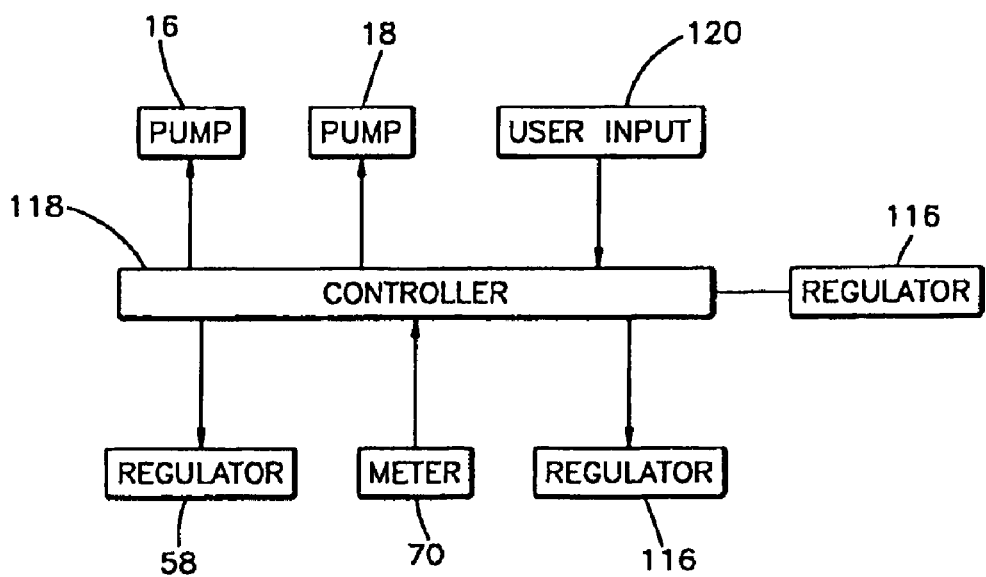
FIG. 4 is a schematic view showing parts of the system of FIG. 3.

Another example of a dialysis system 100 has parts that are shown schematically in FIGS. 3 and 4. Like the dialysis system 10 of FIGS. 1 and 2, the dialysis system 100 of FIGS. 3 and 4 includes distinct hydraulic systems 102 and 104 for dialysate fluid and blood, respectively. Those two systems 102 and 104 have components that are substantially the same as corresponding components of their counterparts 12 and 14 in the dialysis system 10. Such parts are indicated by the use of the same reference numbers in FIGS. 1-2 and 3-4. However, unlike the dialysate fluid system 12 described above, this dialysate fluid system 102 does not have a non-expandable volume that constrains a significant volume of water from passing through the dialyzer membrane 62 from the blood side 64 to the dialysate side 66. Instead, the dialysate fluid system 102 includes a volumetric ultrafiltration system 110.

The volumetric ultrafiltration system 110 includes an ultrafiltrate reservoir 112 which, in the illustrated example, is connected to the third conduit 44 by a fifth conduit 114 with a fluid flow regulator 116. A controller 118 (FIG. 4) is operatively interconnected with the regulator 116 in the volumetric ultrafiltration system 110 in addition to being operatively interconnected with the other control devices that are common to the two dialysis systems 100 and 10. A user input device 120 (FIG. 4) also is included in the volumetric ultrafiltration system 110. Preferably, the controller 118 differs from the controller 80 only by being further programmed or otherwise configured as needed to control the regulator 116 in response to the input device 120 as recited in the claims.

In operation, the controller 118 responds to the input device 120 by actuating the regulator 116 to permit fluid in the system 12 to flow to the ultrafiltration reservoir 112 rather than back to the dialyzer 20. This causes a hydraulic fluid pressure drop on the dialysate side 66 of the membrane 62. The resulting pressure differential acting across the membrane 62 from the blood side 64 to the dialysate side 66 compels water and other blood molecules small enough to move through the membrane 62 to migrate from the blood side 64 to the dialysate side 66.

EXAMPLES

Four examples were run to establish the ability of a mixed bed ion exchange column to control the ionic composition of a solution. The mixed bed ion exchange column used was a PUROLITE PCL-201-1 Mixed Bed Ion Exchange Column manufactured by THE PURLOTE COMPANY (Bala Cynwyd, Pa.). This column had the following characteristics:

Column Dimensions:

| | |
|---|---|
| O.D.: | 2.9" |
| Height: | 9.2" |
| Theoretical Capacity: | 488 grains of NaCl (541 mEq of NaCl) |
| Cation/Anion Ratio: | approximately equal molar amounts |
| Cation Resin: | proton loaded sulfonated spherical styrene-divinylbenzene copolymer |
| Anion Resin: | hydroxide loaded spherical quaternary amine styrene divinylbenzene copolymer |

For each example, a solution was prepared and flowed through a fully charged column. The solutions that were used comprised various ionic species. In each example, the conductivity of the solution leaving the column, i.e., the effluent, was monitored. The example solutions that were prepared contained sodium acetate, sodium bicarbonate, and/or sodium chloride. Solution flow rates were also varied. Solution characteristics and experimental flow rates used in the examples are shown in Table 1.

TABLE 1

Example Parameters

| Example | DFR* (mL/min) | Species Present | Concentration (mEq/L) |
|---|---|---|---|
| 1 | 400 | NaCl | 36.4 |
| 2 | 200 | NaCl | 136 |
| 3 | 400 | NaCl | 136 |
| 4 | 200 | NaCH$_3$COO, NaHCO$_3$, NaCl | 140 |

*DFR = dialysate flow rate

During all runs the temperature of the solution analyzed was maintained at physiologic temperature (37° C.) to simulate use in a dialysis system and because temperature impacts in exchange rates in the column. The solution used during each run was kept well mixed to maintain homogeneous concentration levels. The conductivity of the column effluent was measured using a YSI 3200 conductivity meter manufactured by YSI Incorporated (Yellow Springs, Ohio). The YSI 3200 conductivity meter was also used to monitor the temperature of the dialysate effluent. Data from the YSI 3200 conductivity meter was captured using a computer running software written within VISUAL BASIC 6 (Microsoft Corporation; Redmond, Wash.) and connected to the YSI 3200 through a RS-232 serial port.

Plots showing the experimental results for examples 1 through 4 are shown at FIGS. 5-8. FIGS. 5-8 plot the conductivity (curves 300, 500 and 600) or concentration (curve 400) of column effluent over time. The conductivity/concentration of the solution fed into the column (302, 402, 502 and 602), as shown in each plot, is constant over the course of the experiment because the concentration of the solution fed into the column is constant. In each of the examples shown in FIGS. 5-8, at some point the conductivity/concentration of the column effluent rises above the conductivity/concentration of the example solution, see points 304, 404, 504 and 604. The exact cause of this rise is uncertain. It is hypothesized that this rise is most likely due to an uneven cation and anion loading in the cartridge. The pH was monitored during one example run and the pH dropped during the rise above the conductivity of the example solution. Because of this pH drop and other information provided by the column manufacturer, the anion resin is thought to be the limiting resin.

Figure 5:
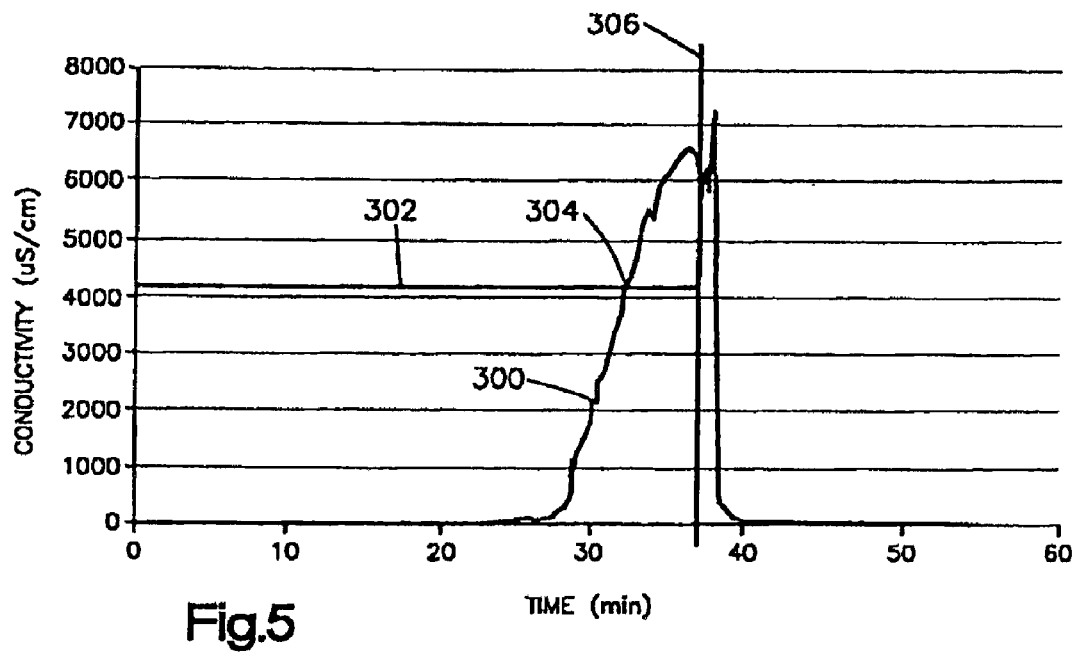
FIG. 5 is a plot of the conductivity of column effluent over time for example 1.

Example 1, as shown in FIG. 5, has an additional experimental parameter over the other experiments. In example 1, at about the time the effluent conductivity peaked, the input solution was switched from the 36.4 mEg/L NaCl solution to distilled water. The perpendicular line 306 indicates the time at which the flow of distilled water was initiated and the flow of NaCl solution was stopped. The conductance of the effluent dropped to about zero shortly after the distilled water flow was initiated as would be expected because the conductivity of distilled water should be about zero. The short delay before the effluent conductance dropped is due to the short length of time it took for the distilled water to transit the column and emerge as effluent. The fact that the effluent conductance dropped to zero when a flow of distilled water was initiated illustrates a feature of the mixed bed ion exchange column used. Specifically, there is no leakage of bound sodium from the column, which makes safe the use of such a column in a dialysis system even if the capacity of the column is exhausted.

Figure 6:
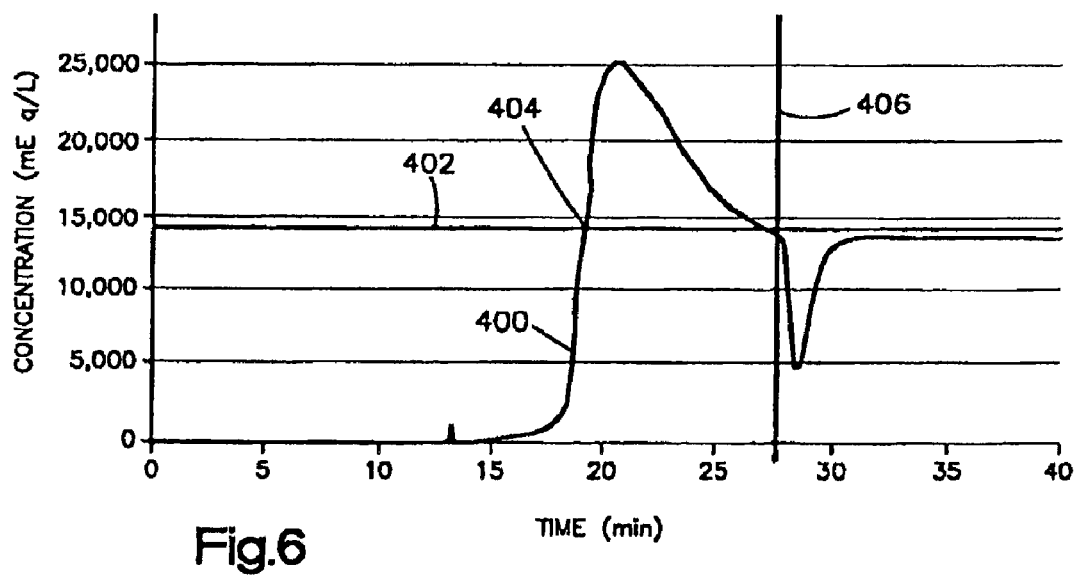
FIG. 6 is a plot of the conductivity of column effluent over time for example 2.
Figure 7:
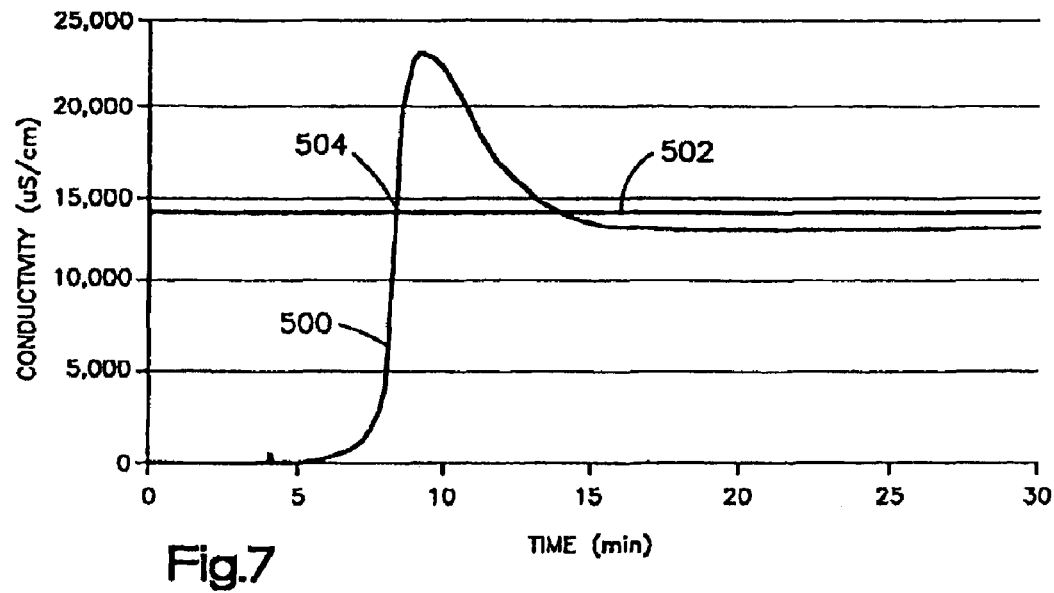
FIG. 7 is a plot of the conductivity of column effluent over time for example 3.

A distilled water flow was not initiated in the remaining three examples. In example 2, as shown in FIG. 6, at about 18 minutes the column capacity was reached and effluent concentration rose. The perpendicular line 406 at about minute 27 marks the time at which the initial supply of NaCl solution was exhausted and a new solution of the same concentration was substituted. As can be seen, the concentration of the effluent rose to about the concentration of the input solution. Example 3, as shown in FIG. 7, shows a conductance curve similar to example 2's concentration curve with the exception that only one NaCl solution was used.

Figure 8:
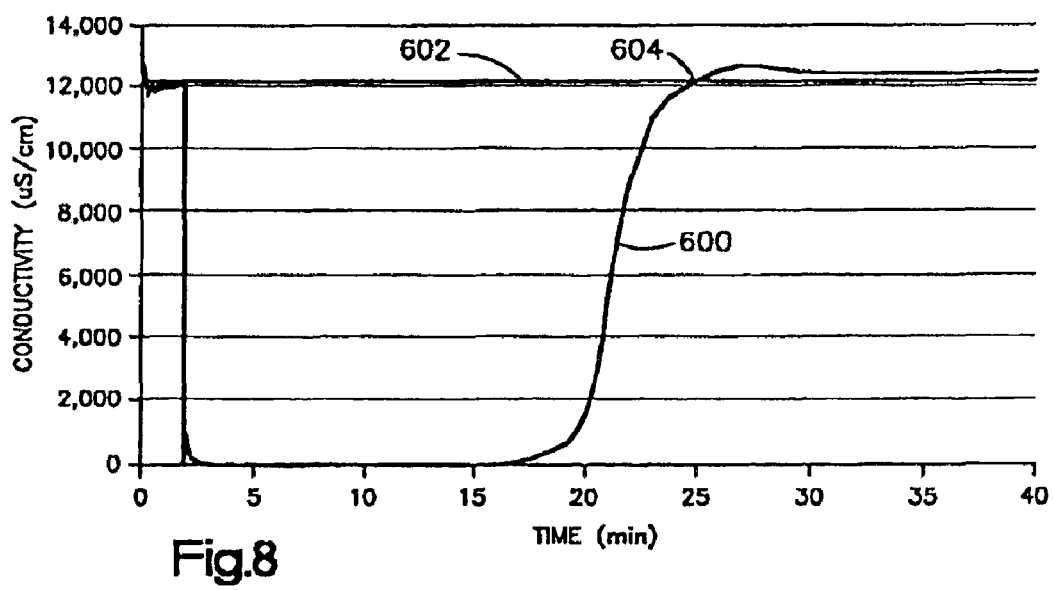
FIG. 8 is a plot of the conductivity of column effluent over time for example 4.

Example 4, as shown in FIG. 8, exhibits a slightly different effluent conductance curve 600 than examples 1-3. In example 4, the effluent conductance 600 does not rise as abruptly past the conductance value for the input solution 602. It is believed that this is most likely due to the presence of sodium bicarbonate in the input solution. With sodium bicarbonate a certain percentage of the sodium is believed to exchange for a proton before the bicarbonate can exchange for hydroxide thereby creating carbonic acid. The carbonic acid can then dissociate to water and carbon dioxide.

The amount of sodium exchanged and the capacity per initial mass of resin for each example is shown in Table 2. In each example, the capacity of the column chosen is less than the theoretical capacity of the column. This level of exchange capacity is compatible with the commercially available SORB+ cartridge manufactured by Renal Solutions, Inc. (Warrendale, Pa.). It has been established by Renal Solutions that 80% of dialysis patients will produce a maximum of about 500 mEq of sodium ions during dialysis using the SORB+™ column. This number is only used here as an indicator of the effectiveness of the technique and columns could easily be provided that have capacities less than or greater than 500 mEq as required by a particular dialysis system. These results demonstrate that a mixed bed ion exchange column, such as the one used by the examples, can be used to remove sodium species from a solution that could be used in a dialysis system as described above. The different input flow rates used in examples 1-4 demonstrate that flow rate had little if any impact on the ability of the mixed bed ion exchange column to adsorb sodium, at least at these flow levels.

TABLE 2

Experimental Results

| Example | Capacity Exchanged (mEq) | Capacity/Initial Mass (mEq/g) |
|---------|--------------------------|-------------------------------|
| 1 | 436 | 0.97 |
| 2 | 506 | 0.97 |
| 3 | 425 | 0.80 |
| 4 | 478 | 0.89 |

This written description sets forth the best mode of the invention, and describes the invention so as to enable a person skilled in the art to make and use the invention, by presenting examples of the elements recited in the claims. The patentable scope of the invention is defined by the claims, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

What is claimed is:

1. A method comprising the steps of:
   a) passing dialysate fluid through a dialyzer;
   b) conveying the dialysate fluid from the dialyzer to a first housing containing material that releases sodium into the dialysate fluid;
   c) passing the dialysate fluid through the material in the first housing;
   d) measuring sodium ion concentration in the dialysate fluid emerging from the first housing; and
   e) conveying the dialysate fluid from the first housing to a second housing containing material that binds sodium ions from the dialysate fluid;
   f) directing a portion of the dialysate fluid to bypass the second housing if the measured sodium ion concentration is not greater than a predetermined level;
   g) passing the dialysate fluid not directed to bypass the second housing through the material in the second housing; and
   h) conveying the dialysate fluid from the second housing and fluid bypassing the second housing back to the dialyzer.

2. The method of claim 1, wherein the predetermined level is about 160 mEq/L.

3. The method of claim 1, wherein the predetermined level is about 155 mEq/L.

4. The method of claim 1, wherein the predetermined level is about 150 mEq/L.

5. The method of claim 1, wherein the predetermined level is about 145 mEq/L.

6. The method of claim 1, wherein the second housing contains a mixed bed ion exchange resin.

7. The method of claim 6, wherein the mixed bed ion exchange resin comprises a cation exchange resin and an anionic exchange resin.

8. The method of claim 7, wherein the cation exchange resin is a sulfonated spherical styrene divinyl benzene copolymer.

9. The method of claim 7, wherein the anion exchange resin is a spherical quaternary amine styrene divinyl benzene copolymer.

10. The method of claim 6, wherein the mixed bed ion exchange resin has a sodium ion binding capacity of less than or equal to about 800 mEq.

11. The method of claim 6, wherein the mixed bed ion exchange resin has a sodium ion binding capacity of less than or equal to about 600 mEq.

12. The method of claim 6, wherein the mixed bed ion exchange resin has a sodium ion binding capacity of less than or equal to about 500 mEq.

13. The method of claim 6, further comprising the step of effecting volumetric ultrafiltration by diverting dialysate fluid into a fluid receptacle.

14. The method of claim 6, wherein the dialysate fluid comprises water suitable for drinking.

* * * * *